(12) United States Patent
Hashiba et al.

(10) Patent No.: US 6,340,762 B2
(45) Date of Patent: Jan. 22, 2002

(54) METHOD FOR OPTICAL RESOLUTION OF PIPERIDINE CARBOXYLIC ACID DERIVATIVE

(75) Inventors: Isao Hashiba; Masami Kozawa, both of Chiba; Kiyotomo Seto, Tokyo, all of (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/802,916

(22) Filed: Mar. 12, 2001

(30) Foreign Application Priority Data

Apr. 13, 2000 (JP) ............................................ 12-112616

(51) Int. Cl.$^7$ ......................... C07D 211/12; C07C 51/00
(52) U.S. Cl. ......................... 546/245; 562/401; 562/471
(58) Field of Search ................................ 546/245, 247; 562/401, 471

(56) References Cited

U.S. PATENT DOCUMENTS

| 4,537,984 A | 8/1985 | Hashiba et al. |
| 4,625,053 A | 11/1986 | Fujinawa et al. |

FOREIGN PATENT DOCUMENTS

| JP | 7-10813 | 1/1995 |
| JP | 7-215922 | 8/1995 |

OTHER PUBLICATIONS

Xiaozhang Zheng, et al., Chirality, No. 7, pp. 90–95, "Synthesis of Stereoisomers of Antithrombotic Nipecotamides", 1995.

*Primary Examiner*—C. S. Aulakh
(74) *Attorney, Agent, or Firm*—Oblon, Spivak, McClelland, Maier & Neustadt, P.C.

(57) ABSTRACT

A method for producing an optically active piperidine carboxylic acid derivative, which comprises subjecting a piperidine carboxylic acid derivative of the formula (1):

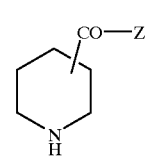

(1)

wherein Z is a protecting group for the carboxyl group, to optical resolution by means of an optical resolution agent of the formula (2):

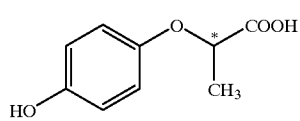

(2)

wherein symbol * indicates that the designated carbon atom is asymmetric.

3 Claims, No Drawings

METHOD FOR OPTICAL RESOLUTION OF PIPERIDINE CARBOXYLIC ACID DERIVATIVE

The present invention relates to a method for optical resolution of a piperidine carboxylic acid derivative.

An optically active piperidine carboxylic acid derivative is an important intermediate for pharmaceuticals (T. G. M. Dhar, et al., J. Med. Chem., 1994, 37, 2334–2342, U.M. Marzec, et al., Arteriosclerosis, 1990, 10, 367–371). Heretofore, optical resolution by means of tartaric acid has been reported as a method for producing an optically active piperidine carboxylic acid derivative. However, in order to increase the optical purity, the obtained tartarate has to be recrystallized repeatedly, thus leading to a decrease in the yield (X. Zheng, et al., Chirality, 1995, 7, 90–95). Further, tartaric acid used for the resolution is likely to be soluble in water, and it is difficult to recover it in many cases, which not only increases the production cost but also is not desirable from the viewpoint of environmental protection. On the other hand, asymmetric reduction of ethyl 1,4,5,6-tetrahydronicotinate has been attempted. However, such is not practical from the viewpoint of either yield (10%) or optical selectivity (24%ee) (H. U. Blaser, et al., J. Molecular Catal. A: Chemical 1999, 139, 253–257).

It is an object of the present invention to provide a method for producing an optically active piperidine carboxylic acid derivative useful as an intermediate for pharmaceuticals, in good yield and with high purity.

The present inventors have carried out an extensive study on a method for producing an optically active piperidine carboxylic acid derivative useful as an intermediate for pharmaceuticals, in good yield and with high purity, and as a result, have accomplished the present invention.

Namely, the present invention provides a method for producing an optically active piperidine carboxylic acid derivative, which comprises subjecting a piperidine carboxylic acid derivative of the formula (1):

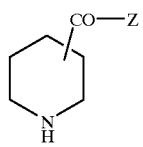

(1)

wherein Z is a protecting group for the carboxyl group, to optical resolution by means of an optical resolution agent of the formula (2):

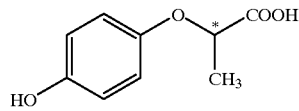

(2)

wherein symbol * indicates that the designated carbon atom is asymmetric.

Now, the present invention will be described in detail with reference to the preferred embodiments.

The protecting group Z for the carboxyl group is not particularly limited so long as it does not hinder the optical resolution agent to form a salt with a nitrogen atom of the piperidine ring, and it may, for example, be an ester or an amide.

As the ester, one wherein the Z moiety in the formula (1) is a $C_{1-12}$ alkyloxy group, a $C_{2-12}$ alkenyloxy group or a $C_{2-12}$ alkynyloxy group, may be mentioned. More typically, the protecting group Z for the carboxyl group may be a $C_{1-6}$ alkyloxy group, a $C_{2-6}$ alkenyloxy group or a $C_{2-6}$ alkynyloxy group. Most typically, the protecting group Z for the carboxyl group may be a methyloxy group, an ethyloxy group, a 1-propyloxy group or a 2-propyloxy group.

As the amide, one wherein the Z moiety in the formula (1) is $NR^1R^2$ (wherein each of $R^1$ and $R^2$ is a hydrogen atom or a $C_{1-12}$ alkyl group, or $R^1$ and $R^2$ may together represent a $C_{3-6}$ saturated or unsaturated alkylene group, which may be substituted by a $C_{1-4}$ alkyl group), $NR^1COR^2$ (wherein each of $R^1$ and $R^2$ is a hydrogen atom or a $C_{1-12}$ alkyl group, or $R^1$ and $R^2$ together represent a $C_{2-5}$ saturated or unsaturated alkylene group, which may be substituted by a $C_{1-4}$ alkyl group) or $NR1COOR^2$ (wherein $R^1$ is a hydrogen atom or a $C_{1-12}$ alkyl group, and $R^2$ is a $C_{1-12}$ alkyl group), may be mentioned. As a particularly preferred protecting group Z for the carboxyl group, an ethyloxy group may be mentioned.

The position of the carboxyl group bonded to the piperidine ring of the compound of the formula (1) to be used in the present invention may be the 2-, 3- or 4-position, particularly preferably the 3-position. As the compound of the formula (1) to be used in the present invention, an ethyl ester of 3-piperidine carboxylic acid is particularly preferred.

The piperidine carboxylic acid derivative of the formula (1) is reacted with the optical resolution agent of the formula (2) in the presence of a suitable solvent, the precipitated diastereomer salt is collected by filtration, and if necessary, recrystallized from a suitable solvent, and then the diastereomer salt is decomposed with an aqueous alkali solution by a conventional method, followed by extraction with a suitable organic solvent to obtain the desired optically active piperidine carboxylic acid derivative.

The solvent to be used for the reaction is not particularly limited so long as the formed salt can be precipitated therein. For example, water, an alcohol (such as methanol, ethanol or propanol), acetonitrile, tetrahydrofuran, chloroform or acetone may be mentioned. As a particularly preferred solvent for the reaction, anhydrous ethanol may be mentioned.

The reaction temperature is not particularly limited so long as it is within a range where the formed salt will be precipitated. It is usually preferably within a range of from −20° C. to 60° C. from the viewpoint of the operation efficiency. Particularly preferably, it is room temperature. The time required for the reaction depends on the precipitation rate of the formed salt, but in many cases, it is sufficient within one day. Particularly preferred reaction time is within a range of from 10 minutes to 6 hours.

The aqueous alkali solution to decompose the diastereomer salt, may, for example, be an aqueous solution of sodium hydroxide, potassium hydroxide, sodium carbonate, sodium hydrogencarbonate or ammonia. Particularly preferred is an aqueous solution of sodium hydroxide, sodium carbonate or sodium hydrogencarbonate. The organic solvent to extract the optically active piperidine carboxylic acid derivative may, for example, be an ether, ethyl acetate, benzene, toluene, chloroform or dichloroethane, and particularly preferred is toluene.

The optical resolution agent of the formula (2) can be recovered without racemization by acidifying the aqueous alkali solution after extraction of the piperidine carboxylic acid derivative, with hydrochloric acid, sulfuric acid or nitric acid, followed by extraction with a suitable organic solvent, and the recovered optical resolution agent can be re-used without purification. The solvent for extraction may, for example, be an ether, ethyl acetate, benzene, toluene, chloroform or dichloroethane. Particularly preferred is toluene.

Now, the present invention will be described in further detail with reference to Examples. However, it should be understood that the present invention is by no means restricted to such specific Examples.

36.7 g of (D)-2-(4-hydroxyphenoxy)propionic acid was dissolved in 70 g of anhydrous ethanol, and 31.5 g of racemic ethyl 3-piperidinecarboxylate was added, whereupon white solid precipitated. To the reaction solution, 675 ml of acetonitrile and 175 ml of water were added, followed by heating at 60° C. to dissolve the white solid, whereupon the solution was left to stand at room temperature overnight. Precipitated colorless crystals were collected by filtration, washed with ethanol and dried under reduced pressure to obtain 21.8 g of a salt of (D)-2-(4-hydroxyphenoxy) propionic acid with ethyl 3-piperidinecarboxylate. The obtained salt was analyzed by liquid chromatography, whereby it was found to be a salt with optically pure ethyl (3S)-piperidinecarboxylate.

To 5.0 g of the obtained salt, 20 ml of ethyl ether and 20 ml of a 20% sodium carbonate aqueous solution were added, followed by stirring vigorously at room temperature for 2 hours. After being left to stand still, the separated ethyl ether layer was taken and ethyl ether was distilled off under reduced pressure to obtain 1.15 g of optically active ethyl (3S)-piperidinecarboxylate (colorless transparent liquid). The optical rotation of the obtained liquid was measured, whereby $[\alpha]_D^{25}=+1.6\pm0.1°$ (c=5, $H_2O$) (value disclosed in literature: X. Zheng, et al., Chirality, 7, 90–95 (1995), $[\alpha]_D^{24}=+1.52$ (c=5, $H_2O$), A. M. Akkerman, et al., Rec. Trav. Chim. Pas-Bas., 70, 899–916 (1951), $[\alpha]_D^{25}=+1.6°$).

What is claimed is:

1. A method for producing an optically active piperidine carboxylic acid derivative, which comprises subjecting a piperidine carboxylic acid derivative of the formula (1):

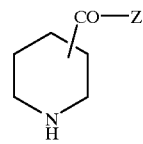

(1)

wherein Z is a protecting group for the carboxyl group, to optical resolution by means of an optical resolution agent of the formula (2):

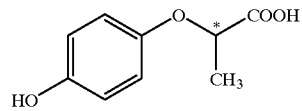

(2)

wherein symbol * indicates that the designated carbon atom is asymmetric.

2. The method for producing an optically active piperidine carboxylic acid derivative according to claim 1, wherein in the compound of the formula (1), the carboxyl group is substituted at the 3-position.

3. The method for producing an optically active piperidine carboxylic acid derivative according to claim 1, wherein the compound of the formula (1) is an ethyl ester of 3-piperidine carboxylic acid.

* * * * *

UNITED STATES PATENT AND TRADEMARK OFFICE
CERTIFICATE OF CORRECTION

PATENT NO.    : 6,340,762 B2
DATED         : January 22, 2002
INVENTOR(S)   : Hashiba et al.

It is certified that error appears in the above-identified patent and that said Letters Patent is hereby corrected as shown below:

<u>Title page,</u>
Item [30], the Foreign Application Priority Data should read as follows:

-- [30]    Foreign Application Priority Data
           Apr. 13, 2000      (JP) ............... 2000-112616 --

Signed and Sealed this

Eleventh Day of June, 2002

*Attest:*

*Attesting Officer*

JAMES E. ROGAN
*Director of the United States Patent and Trademark Office*